United States Patent [19]

Wolf

[11] 4,173,441
[45] Nov. 6, 1979

[54] WEB INSPECTION SYSTEM AND METHOD THEREFOR

[75] Inventor: William E. Wolf, Newark, Del.

[73] Assignee: E. I. Du Pont de Nemours and Company, Wilmington, Del.

[21] Appl. No.: 781,879

[22] Filed: Mar. 28, 1977

[51] Int. Cl.$^2$ .......................................... G01N 21/02
[52] U.S. Cl. ..................................... 356/431; 250/563
[58] Field of Search ...................... 356/200, 430, 431; 250/563

[56] References Cited

U.S. PATENT DOCUMENTS

| | | | |
|---|---|---|---|
| 3,618,063 | 11/1971 | Johnson | 356/431 |
| 3,843,890 | 10/1974 | Anthony, Jr. et al. | 250/563 |
| 3,898,469 | 8/1975 | Nichols | 356/200 |

FOREIGN PATENT DOCUMENTS 2613921 10/1976 Fed. Rep. of Germany.

*Primary Examiner*—Vincent P. McGraw

[57] ABSTRACT

An inspection system for web materials, including electronic means responsive to means scanning the web for detecting a plurality of nonuniform appearance features of the web; means for discriminating these appearance features as to class to identify the significant electrical signal components thereof; means for electrically dividing the web into overlapping areas; means for counting the number of occurrences of the significant signal components over a series of scans within each of the overlapping areas; means for comparing each count with predetermined values to electrically define nonuniform appearance features according to area; and means for combining these nonuniform appearance features to recognize the occurrence of a visual defect class as it occurs within each overlapping area.

3 Claims, 8 Drawing Figures

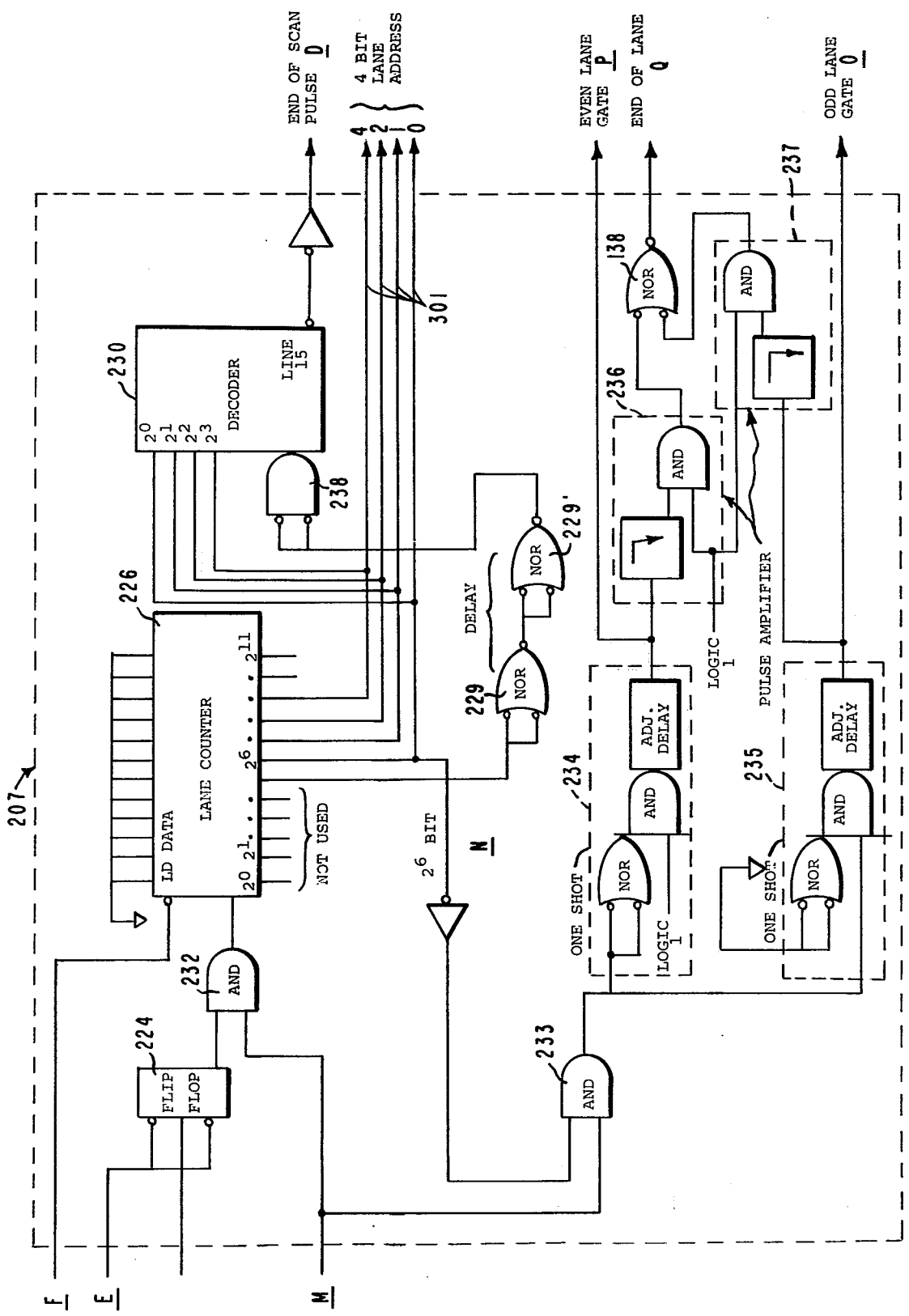

WEB INSPECTION SYSTEM AND METHOD THEREFOR

BACKGROUND OF THE INVENTION

This invention relates to an apparatus and a method for improving the detectability of defects occurring in a moving web. More particularly, it concerns an automatic web inspection system for detecting subtle changes in product optical qualities, identifying which of several types of defects have produced these changes, and locating these defects both in the direction of web motion and transversely thereto.

Although not restricted thereto, this defect monitoring system is particularly applicable to wide webs of nonwoven material manufactured by the process taught by Kinney in U.S. Pat. No. 3,338,992. Several different categories of defects, each identified by its own set of subtle optical characteristics, have been recognized as influencing the ultimate quality of this web material. Furthermore, since many of the defects tend to be localized in areal extent on the sheet material, it is important to be able to locate each defect in two directions, that is, both in the machine direction (MD) and cross machine direction (XD). This information enables the material to be either slit in the MD or cut in the XD to eliminate the defects and salvage the remaining acceptable material.

Many web defect measuring devices are known in the art. For example, Bossons in U.S. Pat. No. 3,803,420 teaches apparatus for detecting and classifying defects into several categories. Geis et al. in U.S. Pat. No. 3,917,414 describe a method and apparatus for monitoring the transverse position of detected defects. Similarly, Akutsu et al. in U.S. Pat. No. 3,958,128 and Nichols et al. in U.S. Pat. No. 3,898,469 teach methods for detecting defects and locating them on predetermined segments across the web material. None of the known inspection systems, however, teach apparatus which generates hypothetical elemental inspection areas (or frames) on the moving web for the purpose of improving the detectability of subtle defects. By making the frame size approximate the defect size, and discriminating each frame separately, signal-to-noise ratios are significantly improved. Furthermore, the extracted signal features from each frame can be used to classify the potential defect into one of several defect categories.

SUMMARY OF THE INVENTION

Applicant's invention includes a laser flying spot scanner system similar to the electro-optical components of the system disclosed by Anthony et al. in U.S. Pat. No. 3,843,890. Such a system is used to analyze the electrical scan signals produced by the photomultiplier tubes located at the ends of the reflection and transmission channel radiation conducting rods and extract a set of signal features which have been found to relate directly to the optical qualities of the corresponding class of defect scanned. In order to enhance the sensitivity of the inspection system to the occurrences of these defects and to provide a means to identify them as belonging to a certain defect category, circuitry is provided to electronically partition the web into a number of inspection lanes, each extending a predetermined number of scans in the direction of product motion or machine direction (MD) to form frames. By means yet to be described, the occurrences of certain single-scan signal features within each lane are counted up at the end of each frame and compared with their corresponding frame thresholds to determine those significant frame features present. A computer is then used to combine the features found within each frame in accordance with Boolean algebraic expressions defining several defect categories in order to identify which, if any, defect category is present and locate it in the machine direction (MD) and cross-product motion or cross machine direction (XD) coordinates.

Selected multiple features of each generated scan signal are extracted by means of multiple discriminator circuits employing predetermined lane feature threshold levels. Discrimination is made not only for one or more amplitude levels above and below a normal but also for signal duration extents for both positive-going and negative-going signals exceeding these levels and for the abruptness of the edges of these positive- and negative-going signals. A computer memory is used to store and then furnish to the discriminators the specific lane feature threshold levels corresponding to the set of predetermined optical characteristics of the specific product styles to be inspected.

Computer and logic circuitry is provided to count scan information over a series of scans before making defect classification and reject decisions based thereon, and comprises means for accumulating in separate sums the several selected feature discriminator outputs in a lane-by-lane basis over the predetermined number of scans separately for each feature to form end-of-frame feature data word sets, e.g., total edge counts per frame.

Furthermore, the computer and logic system includes components for discriminating the end-of-frame feature data words, representative of area type nonuniformities, with respect to their corresponding predetermined end-of-frame feature threshold levels to form binary end-of-frame feature status words. The bits of a feature status word directly correspond to the presence (or extent) of that particular feature in each inspected frame. A computer then combines the several status words generated in each lane in a recognition Boolean algebra statement to effect a defect classification in that lane, categorizes the resulting combination into one of several distinctive defect sets, and generates a lane defect status word together with its XD and MD coordinates.

The electronic portions of this equipment comprise a sophisticated combination of elements that provide inspection analyses of signals from discrete areas of the web, as opposed to its full width, and performs defect discrimination in a manner more analogous to the eye/brain system than does an instrument making a quality decision based on a single scan. This necessitates the use of memory capacity to store a "frame" of data and process this stored "information" to make a quality decision. Quality decisions are made using signal processing circuitry which functions (1) to extract multiple features from each incremental area (frame) scanned, (2) to form binary feature status words having a bit location corresponding respectively to the presence (or extent) of a particularly significant frame feature in the inspection lane, (3) to combine the feature status words by means of Boolean algebraic methods for each individual frame in the web, and (4) to sort the combined feature status words into defect classes or categories for recording and display together with their locations. Furthermore, all steps must be completed between the last scan of the most recent frame and the first scan in the new frame.

Thus an inspection system for web materials is provided that includes electronic means responsive to means scanning the web for detecting a plurality of different nonuniform appearance features of the web, said electronic means comprising: means for electrically discriminating said appearance features so to a predefined class to identify the significant electrical signal components thereof, means for electrically dividing the web into overlapping areas; means for counting the number of occurrences of said significant signal components over a series of scans within each of said areas; means for comparing each count of the number of occurrences of said significant signal components within each area with predetermined values to electrically define nonuniform appearance features according to area; and means for combining said electrically defined nonuniform features to recognize the occurrence of a visual defect class as it occurs within each said scanned area.

This system provides for an improved method of inspecting the web wherein electrical output signals representative of different nonuniform appearance features of the web are discriminated to form extracted single-scan features. The method includes electrically dividing the web into separate overlapping areas; accumulating in separate sums the occurrences of said extracted single-scan features in each said overlapping area; discriminating said separate sums to form binary lane feature status words; combining the bits of said lane feature status words into at least one logic statement, each defining a distinctive defect class; and determining the presence of said defect class according to each said area.

BRIEF DESCRIPTION OF THE DRAWINGS

FIG. 2A is a circuit diagram of the lane gate generator circuit;

DETAILED DESCRIPTION OF THE PREFERRED EMBODIMENT

Figure 1:
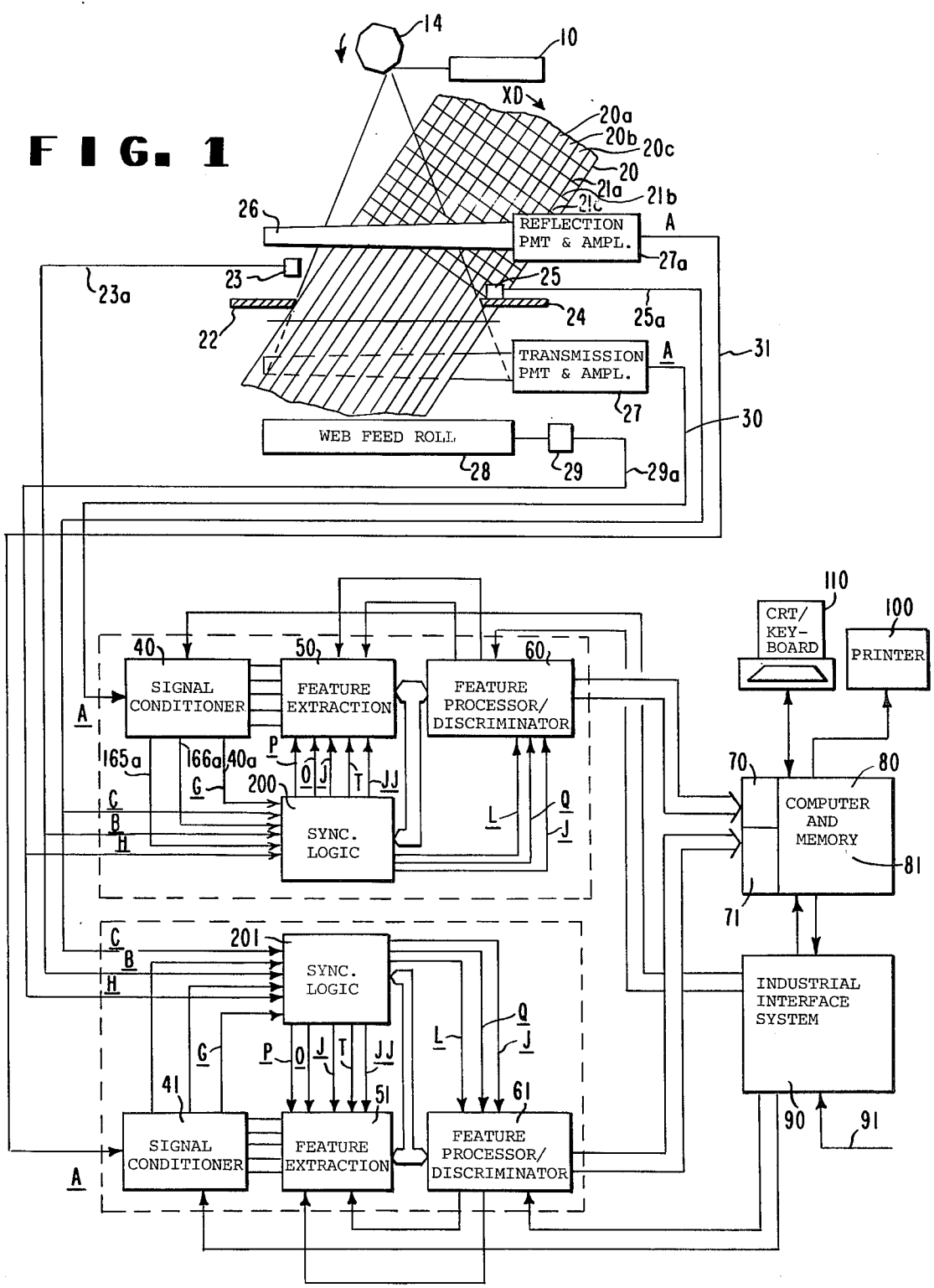
FIG. 1 is a general system block diagram.

This inspection system employs a laser scanner constructed substantially as disclosed by Anthony et al. in U.S. Pat. No. 3,843,890. FIG. 1 provides a schematic representation of the scanner used in the present system. The major components of the scanner are a laser 10, typically a Hughes, Inc., 10 mW HeNe type. The laser beam is focused by optics and directed toward the face of a rotating mirror 14, typically one having twelve equal flat faces. The mirror is driven by a hysteresis synchronous motor not shown. This motor is supplied by a crystal controlled inverter to provide motor speed of 8000 rpm, accurate to within 0.01%. A scan period of 625 microseconds is provided as the beam is reflected onto moving web 20.

A first movable curtain 22 is arranged above and near one edge of web 20 and has fixed above it to the scanner frame a photocell 23. Similarly, a second movable curtain 24 is arranged near the other edge of the web with a second edge photocell 25 fixed thereto.

A first radiation rod collector 26 is located underneath the web to receive transmitted light. Collector 26 furnishes light to a photomultiplier tube located in housing 27. A similar collector 26a and photomultiplier tube located in housing 27a are located above the web to provide for collecting and transducing reflected light from the top surface of the web. Each photomultiplier tube is provided with a preamplifier, not shown, which contains internal automatic gain control that maintains a constant average pedestal voltage for the signal output of each channel at approximately one volt.

A web feed roll 28 provided with a drive mechanism, not shown, feeds the web past the scanner. A shaft motion encoder 29 coupled to roll 28 provides a signal which is employed in the system electronics for enabling operations, for locating defects in the MD direction, and for segmenting the web electronically into the inspection frames as described below.

Thus, both reflection and transmission video signals are provided for analysis by the electronic equipment to be described. The reflection channel is useful in detecting surface flaws and nonuniformities, whereas the transmission channel is mostly useful in detecting defects which are identified by substantial changes in basis weight in the material.

Output cables 30, 31 from the transmission and reflection channel detectors, respectively, connect to their individual signal conditioning subsystems 40, 41. These are followed by signal extraction elements 50, 51 and feature processor/discriminator components 60, 61 which in turn are connected through interface systems 70, 71 to a computer and disc memory combination (typically a Digital Equipment Corp., PDP-8E computer 80 and RKO-5 disc memory unit 81). Combination 80, 81 is first interconnected with an industrial interface system 90 (typically a DEC UDC-8) comprising logic elements arranged to decode and then transmit digital threshold information (having been introduced by means of keyboard 110 through computer/memory 80/81) to the signal conditioning subsystems 40, 41 and corresponding feature processors/discriminators 60, 61. After receiving over input cable 91 information concerning roll weight, yardage, and process signals from remote stations, industrial interface system 90 encodes this information into a binary format and transmits it to the computer/disc memory combination 80, 81. A line printer 100 and a keyboard input device 110, equipped with a cathode ray tube (CRT) display unit, communicates with the computer.

One of the primary requisites of this system for inspecting wide webs is that defects be located in both machine direction (MD) and transverse direction (XD) coordinates. Furthermore, the detection and location scheme must include cases where multiple defects may be overlapped. This is accomplished by "dividing" the width of web 20 electronically into typical 10" (25.4 cm) wide, overlapping parallel lanes 20a, 20b, 20c that extend in the MD. In the case of a 160" (406.4 cm) wide web, 16 inspection lanes would be used. Frames are formed by partitioning each lane into lengths 21, 21a, 21b, 21c, etc., each extending typically 12" (30.5 cm) in the machine direction (MD). Hence the product is inspected in 10"×12" (25.4-30.5 cm) rectangles as indicated on web 20.

Figure 2:
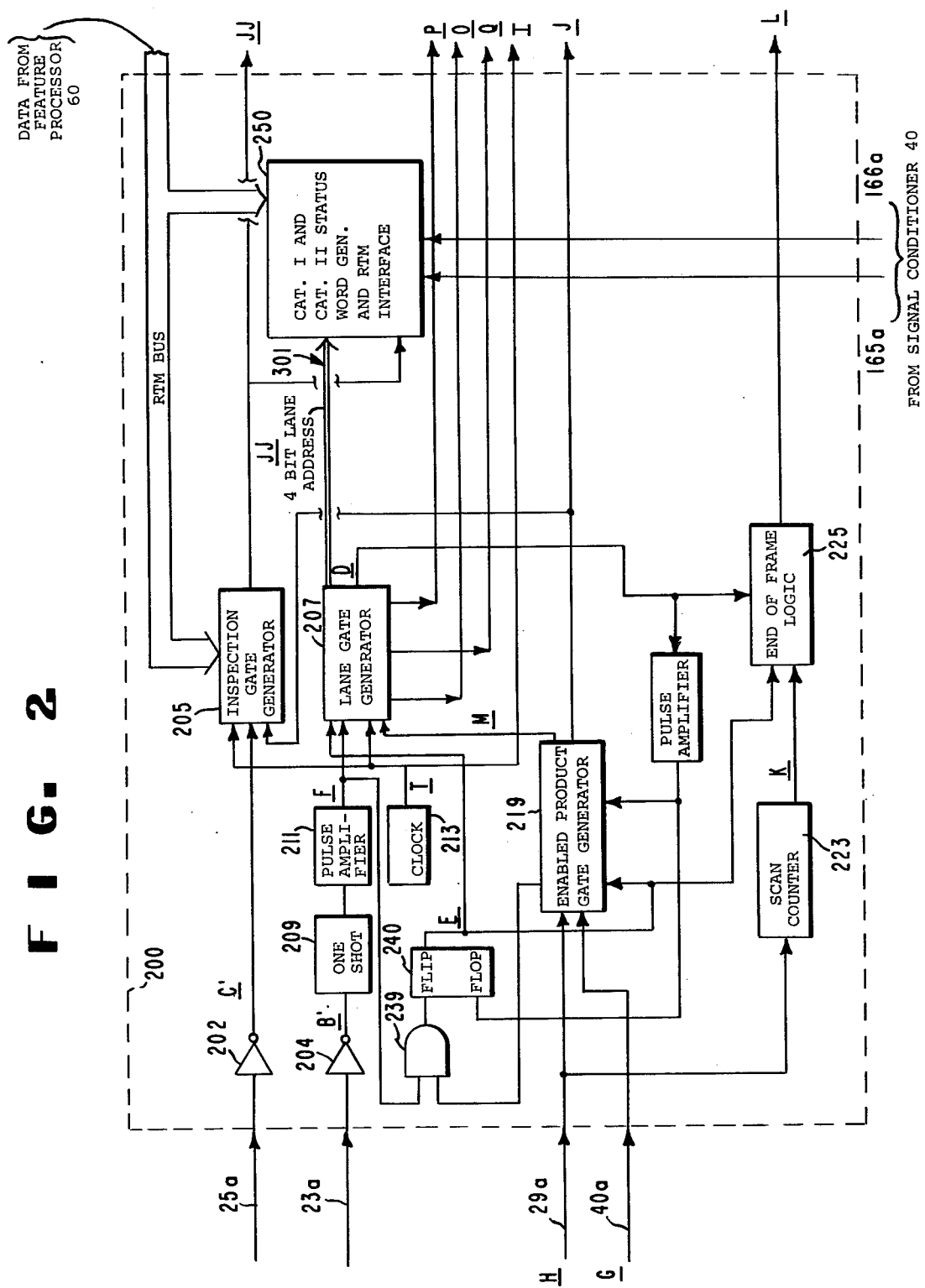
FIG. 2 is a block diagram of the synchronization logic and system gating circuit.

Since the frame dimensions are formed electrically, rather than optically, one can easily change frame XD and MD dimension size simply by using different output positions on two digital counters contained within synchronization and logic circuit 200. The method for doing this will be clear in the following description:

Electronic partitioning of the web, first into a set of lanes and then further into frames, is accomplished by the gate generating circuits contained in the gating and synchronization logic circuit 200, 201 of FIG. 1 and detailed in FIGS. 2 and 2A. More specifically, lane gate generator 207 and end of frame generator 225 are used to provide the partitioning and allow the lane overlap to ensure that defects straddling lane boundaries are detected. Turning to FIGS. 1, 2, 2A and 7, photocell 23 produces a pulse B at the start of each scan which is then applied to pulse shaper 204 via line 23a to produce an inverted digital pulse signal waveform B'. Pulse shaper 204 consists of an operational amplifier and comparator driving a TTL gate to produce a standard TTL pulse. This signal is applied to the input of one shot 209, typically a Fairchild type 9602, which in turn produces a signal needed to trigger pulse amplifier 211 such as a DEC M606 to produce clear 1 signal, waveform F. The clear 1 signal, waveform F, is used to initialize lane counter 226, FIG. 2A, at the start of each scan. A crystal controlled clock 213 (e.g., DEC type M405) is connected to the CLK terminal of J-K flip-flop 224 via line T. Flip-flop 224 is used to divide the clock rate by 2 during each scan interval as controlled by scan gate E, applied to both data in and reset terminals. The crystal controlled clock signal T, is combined with the lane gate generator enable signal M by AND gate 232 to increment lane counter 226. Lane gate generator enable signal, waveform M, generated by the enabled product gate generator 219 is used to delay the clock signal to lane counter 226 to ensure the starting edge of lane 1 lies within the unmasked portion of light conducting rod 26. Each lane is 128 clock counts wide, but the count is divided by means of flipflop 224, hence the bit 6 terminal on lane counter 226 will change state every 64 input counts giving a pulse train, waveform N, of the proper duration for generating odd and even lane gates waveforms O and P, respectively. The bit 5 signal which occurs at the end of each lane is transmitted over line 228 from counter 226, through OR gates 229 and 229' and impressed on 1 in 16 decoder 230 (e.g., DEC M155) at strobe input terminals 232. Gates 229 and 229' are used to provide a delay for this signal. Upon detecting the change in state of the 16th line (labeled line 15 in FIG. 2A), decoder 230 generates an end of scan pulse, waveform D, which in turn is used to terminate lane gate generator enable signal waveform M, thus preventing the generation of additional lane gate signals during that scan. Note that the lane address lines 301 from lane counter 226 identify the number of the lane which is currently being scanned and transmit this information to a decoder in the CAT I and CAT II status word generator circuit 250 (FIG. 2). These status words are transmitted to the feature processor/discriminator 60/61 via the RTM bus system on command, see FIG. 5, Task 12, 404.

Turning to FIG. 2A, bit 6 signal waveform N, from lane counter 226 is input to AND gate 233, with lane gate generator enable signal, waveform M, controlling, to generate odd (odd numbered lane) and even (even numbered lane) gating signal trains waveforms O and P, respectively. One shots 234 and 235, which are connected to the output terminal of AND gate 233, are each adjusted to provide predetermined overlaps between the trailing edges of the even and odd gate pulses and the leading edges of their opposite numbers. The degree of overlap, illustrated in waveforms O and P of FIG. 7, can be adjusted from 0" to 3" (0-7.6 cm) by changing the delay times of one shots 234 and 235; these operate alternately to produce an end of lane signal Q through OR gate 138, upon the occurrence of the trailing edge of either one or the other lane gate signal. Referring to FIG. 2 signal C from photocell 25 is applied to the pulseshaper 202 via line 25a. Pulseshaper 202 is identical to pulseshaper 204 and similarly converts the photocell pulse signal to a TTL pulse, C'. This standard TTL pulse is applied to inspection gate generator 205. Signal H from the motion encoder 29 (typically a Type 80 manufactured by DYNAPAR Corp.), is a TTL logic pulse, which enters synchronization logic circuitry 200 on wire 29a and is applied to enabled product gate generator 219. Circuit 219 produces several enabled gate signals based on the occurrence of the motion pulse signal. Each motion pulse H produces a flag signal of equal duration that together with the occurrence of a clear 1 signal F at the start of each scan operate through AND gate 239 to toggle flipflop 240, and thus generate scan gate signal waveform E. Flipflop 240 is reset at the end of each scan by an end of scan signal D produced by lane gate generator 207. In addition, product gate signal G enters circuit 200 on wire 40a from signal conditioner 40 and is applied to enabled product gate generator 219. These two signals are combined in enabled product gate generator 219 using standard TTL logic elements to develop an enabled product gate signal J, and a lane gate generator enable signal M which occur in synchronism with each transit of the laser scan across the product plane. Only one enabled product gate (signal J) is generated per each motion encoder pulse (signal H). Signal J is also applied to inspection gate generator 205. Inspection gate signal JJ produced by gate generator 205 is a standard TTL logic signal which occurs as the laser scan transits the product in the inspection zone. It is delayed so that its start occurs after the start of the enabled product gate signal J, as shown in the timing diagram FIG. 7. Motion encoder pulse H is also applied to scan counter 223. Since the output from scan counter 223 is a TTL pulse which occurs after each set of a predetermined number of motion pulses have occurred, these counts also correspond with the number of enabled product gate signals J that have been generated. End of frame logic generator 225 connected to scan counter 223 (DEC M236) simply generates a TTL logic pulse waveform K after the desired number of enabled scans have occurred. End of scan signal D generated by the lane gate generator 207, and scan gate signal E are also applied to end of frame logic 225 to ensure that end of frame pulse L occurs only after the end of the last enabled scan of the sequence. Scan counter 223 and end of frame logic 225 consist of collections of standard TTL logic elements, typically those manufactured by the Digital Equipment Corp. as M logic type series circuit boards. The design of inspection gate generator 205 is slightly more complex in that it is an adaptive type circuit. It generates an inspection gate JJ which adapts itself to always remain inside the enabled product gate J. This adaptive feature is accomplished using a circuit comprising Digital Equipment Corp. RTM logic modules which measures each enabled product gate duration, waveform J, and then computes the duration of the corresponding inspection gate, waveform JJ, based on the measured values. More specifically, the RTM circuit arithmetically computes gate size by modifying a final upcount tally of clock 213 counts which have occurred within the duration of each enabled product gate. This modified value is then used as the inspection gate width in the next enabled scan cycle. Thus changes in the duration of the enabled product gate are continually followed by the inspection gate generator on an automatic basis. Synchronization logic circuitry 201 is nearly identical in design and implementation to the system 200 just described.

Figure 3:
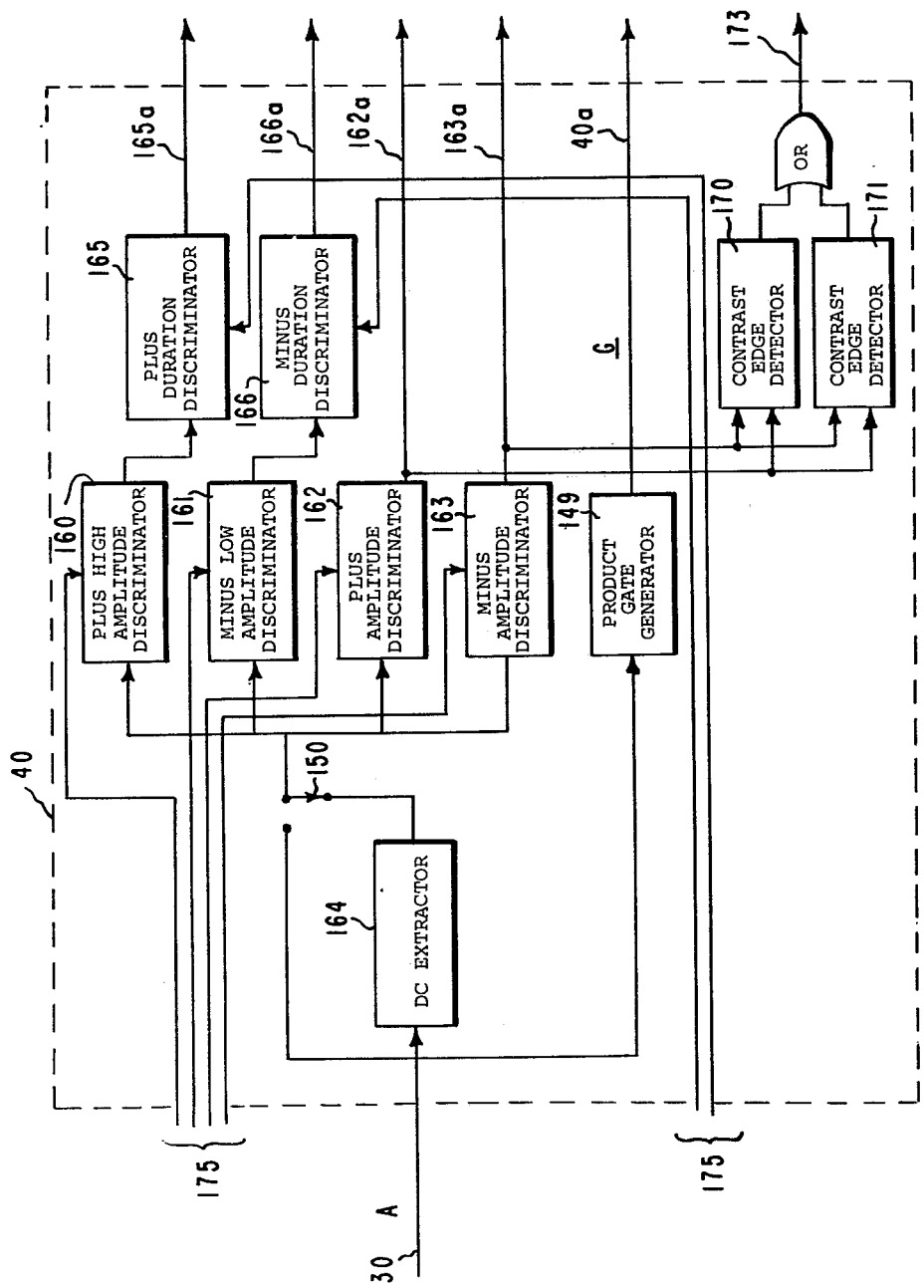
FIG. 3 is a block diagram of the signal conditioning circuits.

The signal conditioning system 40 (FIG. 3) and its counterpart 41 are identical in design and implementation. Where signal conditioner 40 operates on the transmission signal, signal conditioner 41 operates on the reflection signal. Signal A from amplifier 27 enters signal conditioner 40 over line 30 where it can be processed either through DC extractor circuit 164, fully described in U.S. Pat. No. 3,866,054, or bypass the DC extractor completely dependent on the position of switch 150. The plus high amplitude discriminator 160 and duration discriminator 165 circuits have been previously described in the above mentioned U.S. Pat. No. 3,886,054. The plus and minus amplitude discriminators 162 and 163, respectively, are standard integrated circuit discriminators and develop TTL compatible pulses whenever the amplitude of an input signal exceeds a prescribed threshold. Signal lines 175 entering the signal conditioning unit 40 carry threshold levels generated by the computer system. Contrast edge detector circuits 170 and 171 are described in U.S. Pat. No. 4,011,457. The output signals from signal conditioning unit 40 consist of a Category I pulse which occurs whenever a hole or thin spot greater than a given dimension is detected in the web 20, and a Category II pulse which occurs whenever a thick spot greater than a given dimension is detected. Positive and negative amplitude above threshold pulse signals are generated over lines 162a and 163a, respectively, when the amplitude of the signal exceeds positive and negative amplitude threshold settings. Product gate signal G, which is developed by product gate generator 149, is a TTL logic pulse having a duration corresponding to the length of time it takes the laser scan to travel the unmasked length of the rod collector (or to cross the product plane). The circuits used in signal conditioning system 40 are all commercially available integrated circuits or circuit cards manufactured by Digital Equipment Corporation. The signals generated by signal conditioner systems 40 and 41 are applied to feature extraction systems 50 and 51, respectively.

Figure 4:
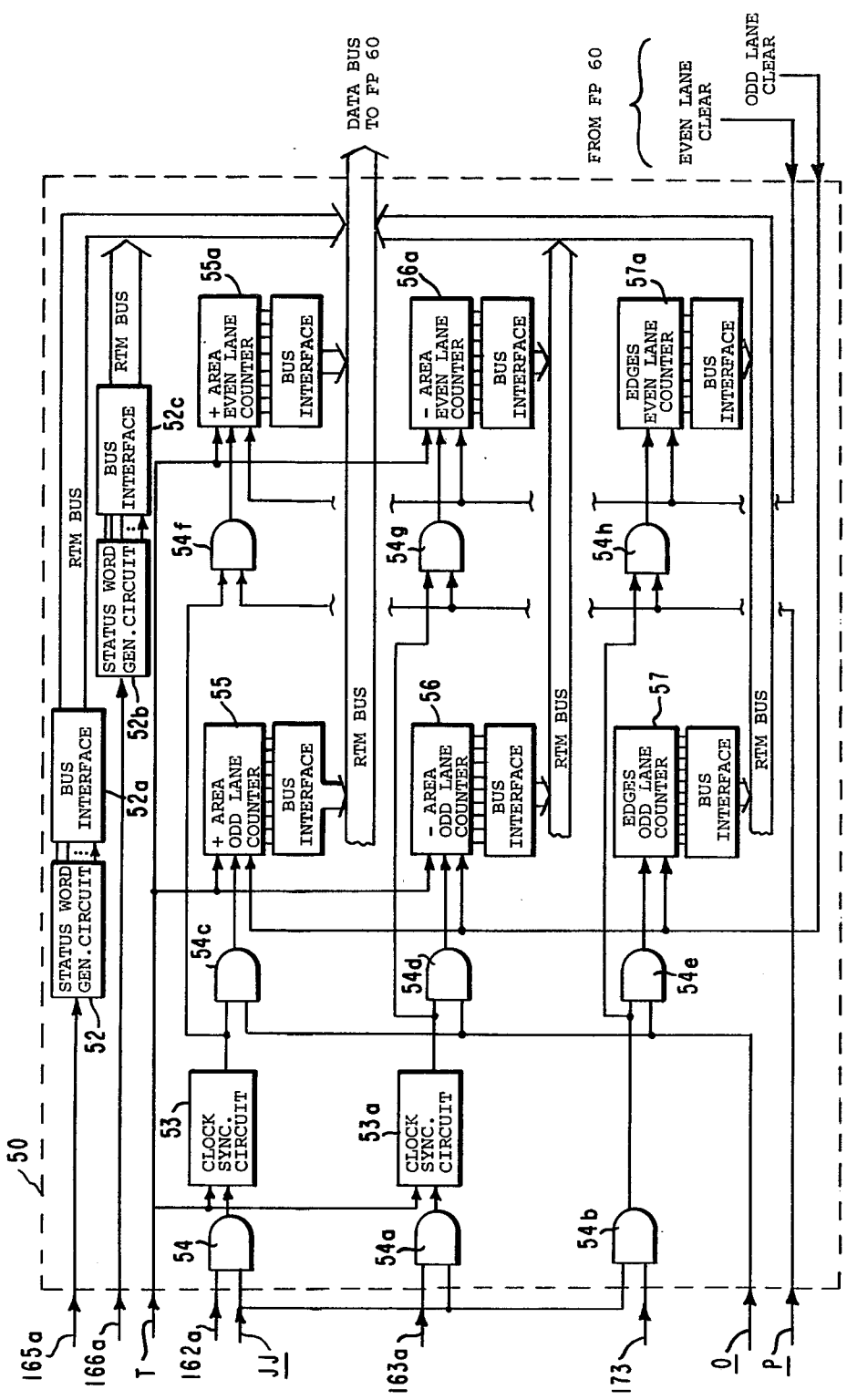
FIG. 4 is a block diagram of the feature extraction signal processor.

Feature extractor circuits 50 and 51, which are identical in design and implementation, are used to convert the pulse data received from the signal conditioner units into digital information for further processing by the feature processors 60 and 61. Referring to FIG. 4, the Category I pulses are applied to a status word generator circuit 52 from duration discriminator 165 via line 165a. This status word generator circuit generates a status word containing bit information locating Category I defects in the proper lane of the web as they occur. In an indentical manner, the Category II pulses are applied to a status word generator circuit 52b from duration discriminator 166 via line 166a which also generates a status word containing information about the presence and location of Category II type defects in the web. The outputs of plus amplitude discriminator 162 and minus amplitude discriminator 163 are applied to clock synchronization circuits 53 and 53a via lines 162a and 163a and thence to odd and even lane (+) and (−) area counters 55, 55a, 56, 56a, respectively, through AND gates 54c, 54f, 54d and 54g, respectively. Odd lane gate signal O and even lane gate signal P are applied to gates 54c and 54f, to steer the plus amplitude information into the proper lane counter, based on whether an even lane or odd lane is being inspected. In a similar fashion, gates 54d and 54g steer the minus amplitude information to the appropriate lane counters. The area counters count the number of clock pulses I that occur during the intervals that the discriminators are in the active state. Thus, at the end of each lane, a lane count is stored in each counter. This lane count is then transferred to the feature processor 60 via the RTM bus interface and the RTM bus upon receipt of its respective lane clear signal. The edge pulses enter feature extraction unit 50 over line 173 and are steered to lane counters 57 and 57a in a manner exactly the same as for the area counters. Similarly, at the end of each inspection lane, this data is transferred to the feature processor via the bus interface units.

Figure 5:
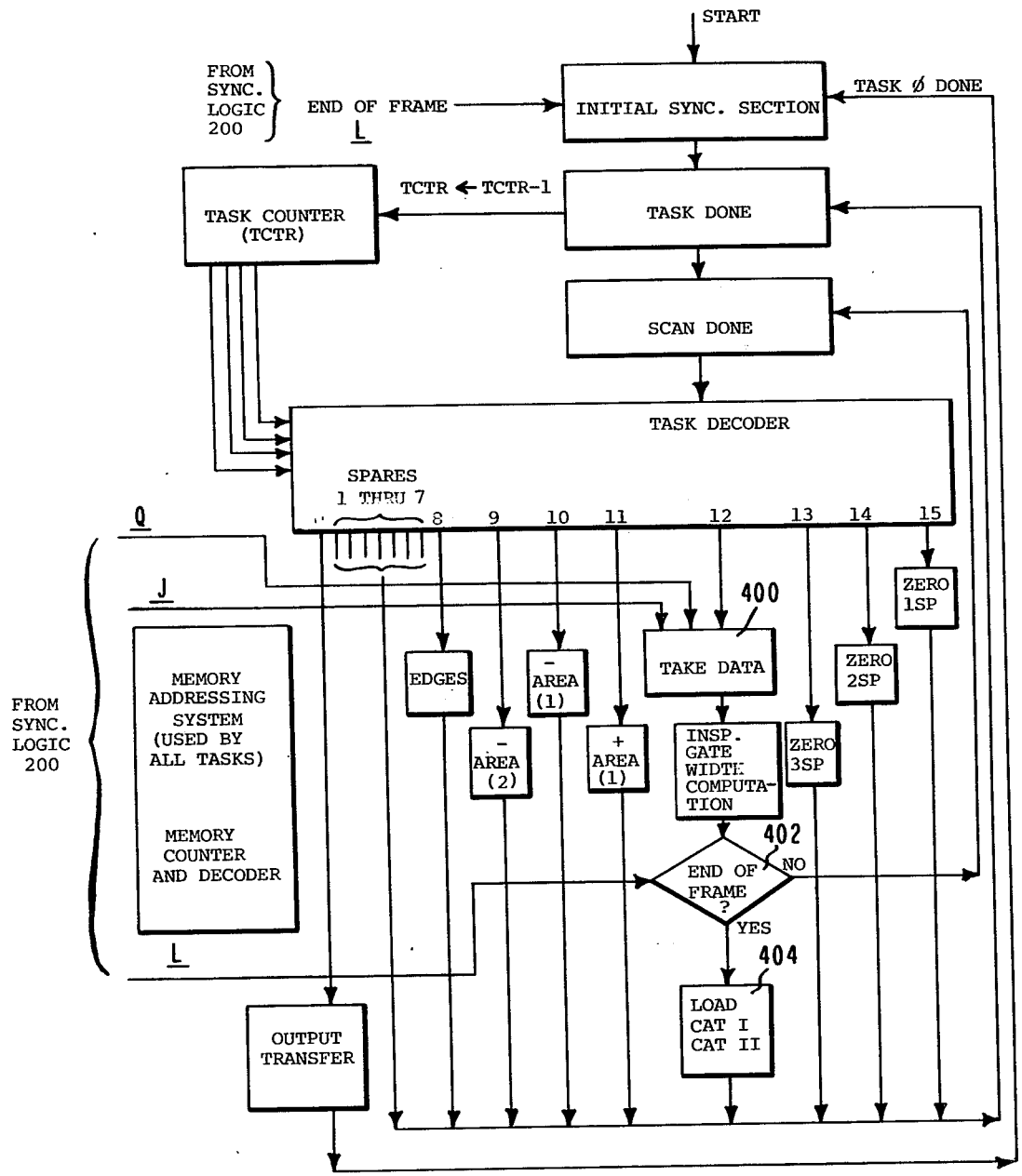
FIG. 5 is a block diagram showing an arrangement of RTM logic elements used to implement even and odd lane signal processing.
Figure 6:
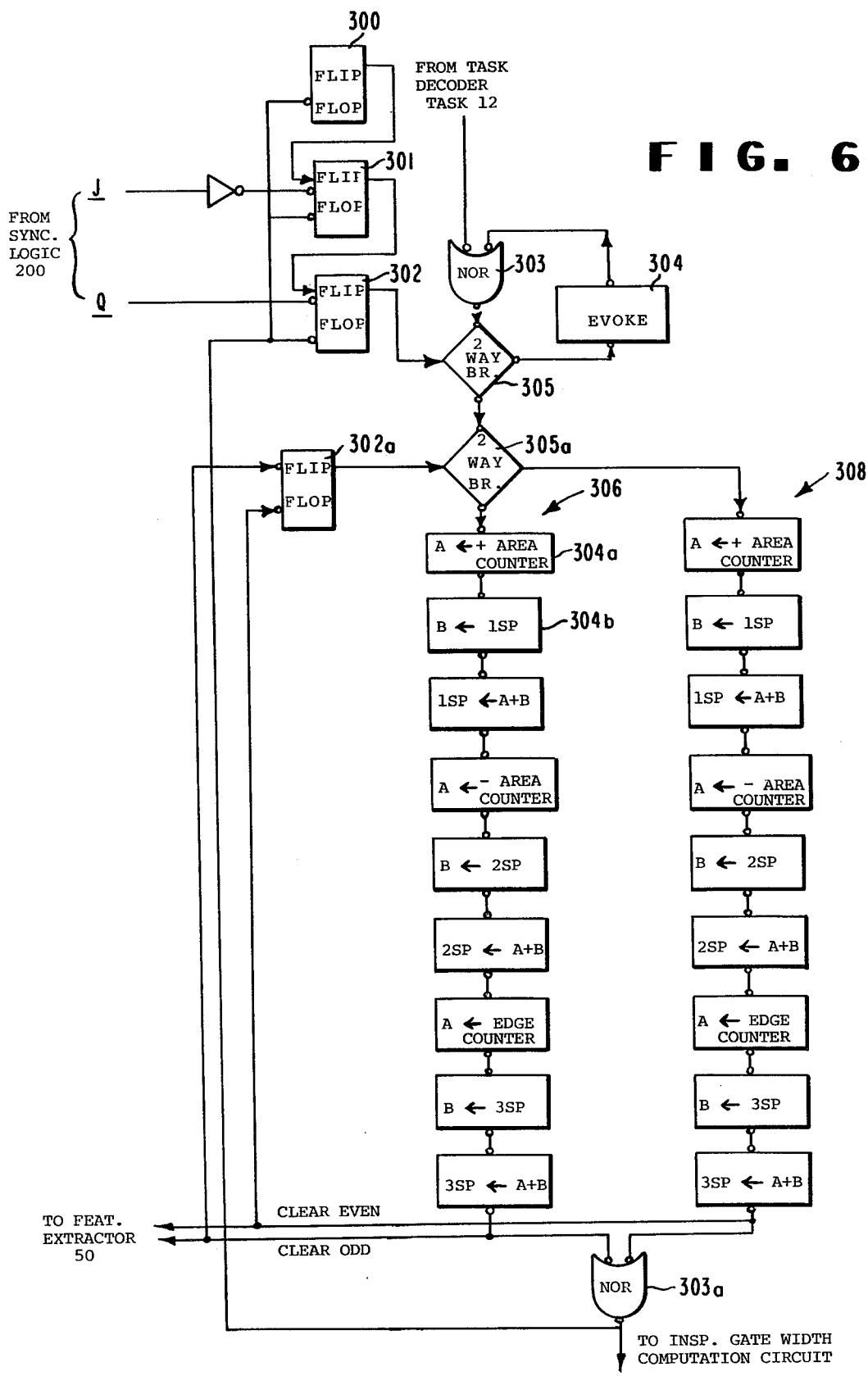
FIG. 6 is a block diagram showing the assignment of extracted features to even and odd lane RTM circuits.
Figure 7:
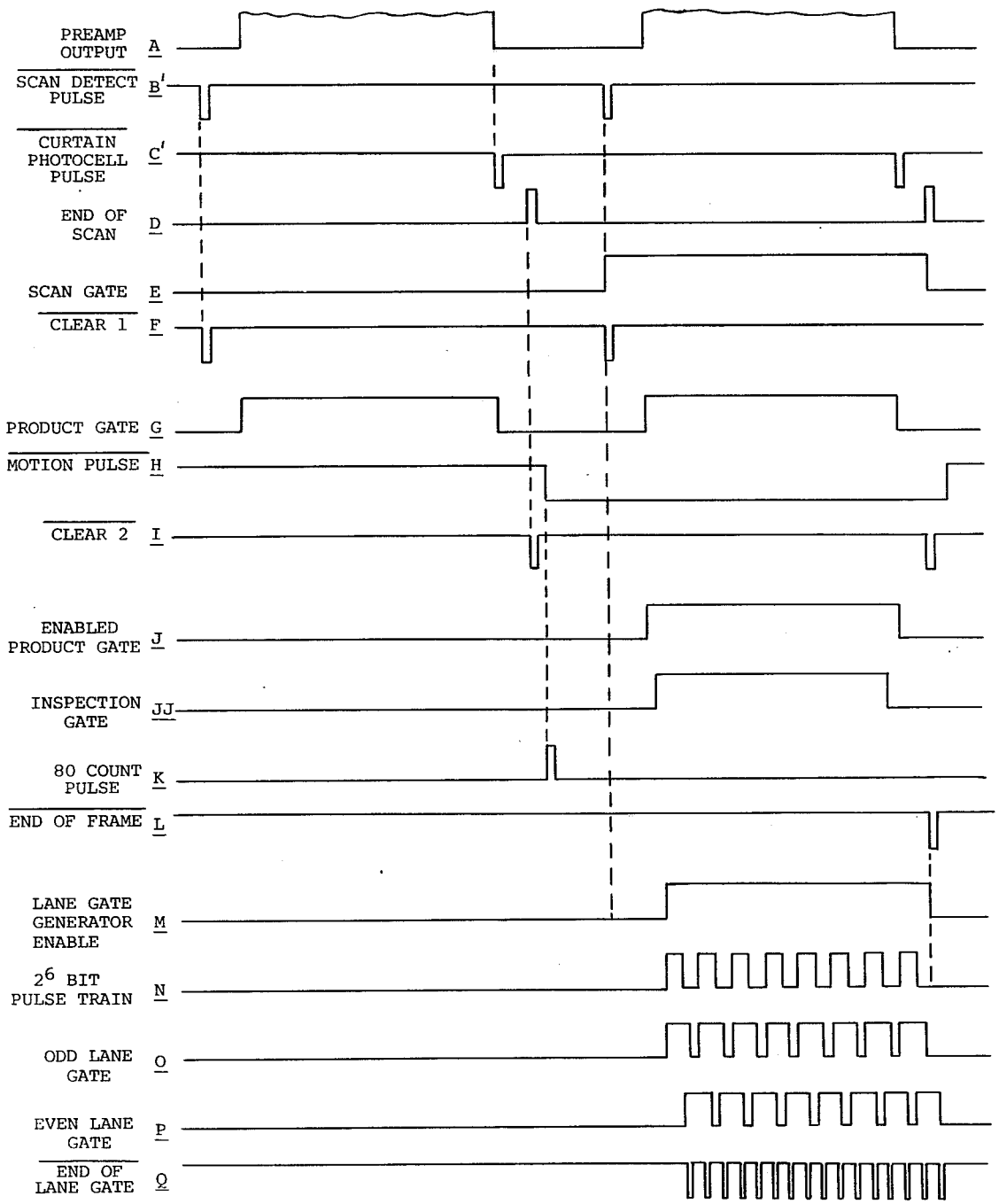
FIG. 7 is a signal timing diagram for the system showing signal wave forms appearing at designated locations in the Figures.

The circuitry for feature processor/discriminator unit 60 and its counterpart unit 61 is shown schematically in FIG. 5. The representation shown in FIG. 5 is a flow chart of the feature processor/discriminator unit which is made up of Digital Equipment Corporation RTM circuit modules. The actual physical connection of these modules can best be described by a flowchart using the procedure described in Bell, Grason and Newell, "Designing Computers and Digital Systems", Digital Press, 1972, and developed by Digital Equipment Corporation. FIG. 5 shows an overall flow diagram in abbreviated form that describes all the functions performed by the feature processor/discriminator during one frame of operation of the inspection system. One frame consists, in this particular instance, of eighty enabled laser scans. Feature extraction unit 50 feeds data into feature processor unit 60 by way of the take-data operation block 400 shown in FIG. 5. Note that the take-data operation 400 is designated as Task No. 12 and end of lane pulse Q and enabled product gate J are used as synchronization pulses for the take-date operation. FIG. 6 is a flow diagram of the take-data operation shown in RTM notation. This notation prescribes not only the actual RTM hardware needed but also how the modules are interconnected to perform the task. For example, flipflop 300 is an M7306 flag module. Similarly, elements 301, 302 and 302a are all standard flip-flop or flag modules. Elements 303 and 303a are negative OR gates and element 305 is an M7312 two-way branch module all of which can be purchased from Digital Equipment Corporation. The boxes containing operational statements such as element 304 are DEC Type M7310 evoke modules. The interconnecting lines define the wiring necessary to properly connect these modules to function in the sequence shown. For example, evoke module 304a performs the operation of storing the contents of (+) area odd lane counter 55 (FIG. 4) in register A. As the RTM system steps through the odd lane sequence, indicated generally by 306, it take the contents of counter 55, stores it in register A and proceeds to the next evoke module, element 304b.

Evoke 304b causes the contents of memory location 1SP to be deposited in register B. In the next operation, the sum of the two registers A and B is stored into memory location 1SP. Following the evoke string, additional summing operations take place for the (−) area and edge counters, respectively. The second sequence, generally indicated as 308, operates identically to the first on even lane generated data. By alternating operations the two sequences process odd and even lane data and then store these data into the designated memory locations for read out at the end of each frame. The memory locations then contain the summed features, such as positive area $+A_l$, negative area $-A_l$, and edge count $E_l$ for each frame in each of the sixteen lanes. A two-way branch element 402 (FIG. 5) is located in the Task 12 string which determines the next step in the program based on whether end of frame signal L from end of frame logic element 225 (FIG. 2) has occurred. In the event that an end of frame signal has occurred the contents of the Category I and Category II registers 404 are loaded into the feature processor and the loop continues on to the task done step at which time the task counter is decremented to the next task, which in this case would be No. 11. Task 11 determines whether the summed positive area exceeds the positive area threshold value. Should the threshold be exceeded, a bit is set in the status word, indicating which lane contains an area that exceeds the threshold. Task 10 is completed in a similar fashion for negative areas. Similarly, Task 9 compares negative areas with a second threshold distinctive from the first. Task 8 performs the same operation on the edge count. Tasks 1 through 7 are spares, no function being performed there. Task $\phi$ transfers the feature status words generated within the RTM computing system to the general purpose computer 80. Other tasks performed by the RTM system such as 15, 14, and 13 are simply routine bookkeeping chores of zeroing all memory locations between frames to insure that only counts obtained from the frame being inspected are accumulated in each frame tally. Elements 70 and 71 shown in FIG. 1 are interface circuits to permit connection of the RTM feature processor/discriminator units 60 and 61, respectively, to the mini computer 80 system bus. Elements 70 and 71 are typically Digital Equipment Corporation M1703 circuit boards.

In operation, the feature extraction circuitry extracts selected features from the product pedestal signal A and converts these features to digital form for transfer to its associated feature processor during each scan. These signal scan features may include, for example:

(1) positive high amplitude and time, $C_{1l}$ (the number of times signal has exceeded both positive amplitude and duration thresholds in each lane during scan).

(2) negative high amplitude and time, $C_{2l}$ (same as above, but for negative amplitude and duration thresholds).

(3) positive low amplitude count/scan, $+a_{nl}$ (the number of times signal has exceeded positive low amplitude threshold values in each lane during scan).

(4) negative low amplitude count/scan, $-a_{nl}$ (same as above, but for negative low amplitude thresholds).

(5) contrast edge count/scan, $e_{nl}$ (number of times signal amplitude has made a rapid (+) to (−) or (−) to (+) transition in each lane during scan).

A detailed description of the size discriminator means used to generate the $C_{1l}$ and $C_{2l}$ signals is found in previously mentioned U.S. Pat. No. 3,866,054. In general, it will detect those nonuniform regions of the web which exceed both contrast and areal extent criteria such as holes, wrinkles, and spots.

The edge detection circuits take the form described in U.S. Pat. No. 4,011,457. The two edge detector circuits are provided in order to detect edges arising from transitions from lightweight to heavyweight and from heavyweight to lightweight areas, accordingly.

The feature processor/discriminator circuits 60, 61 are high speed digital computer circuits that are arranged to perform a fixed program within a cycle time of less than 1 microsecond. Basically, the function of this circuitry is to collect scan by scan feature information generated by feature extractors 50, 51, accumulate these data, and after discrimination arrange it into a frame format acceptable for input to computer 80 to enable it to make a defect decision and record it before the next frame of scans commences. Its operation can be followed best by reference to an example:

The positive low amplitude count/scan, $+a_{nl}$, data are summed over a sequence of eighty inspection scans across sixteen lanes, to provide a positive low amplitude count per frame, $+A_l$, for each one of the lanes scanned. Since the value of $+A_l$ is proportional to the positive portions of the scan signal area above threshold appearing in frame l, the system can compare this value with the positive area threshold, $+A$, furnished by the industrial interface 90 and cause a logic 1 to be set into the l-th bit position in the area feature status word register in the event $+A_l$ exceeds the threshold, $+A$. The feature status words, corresponding to the frame features remaining to be determined, are found in a similar way. After each status word is composed, it is sequentially transmitted to the computer, which arranges the data into one or more Boolean algebraic statements to make a defect category decision. For example, a logic statement defining a Category III (blow-around or curl) defect is:

$$(E_l) \text{ and } (+A_l \text{ or } -A_l) = C_{3l}$$

This says that if the number of edge occurrences per frame, $E_l$, and either the positive signal area $+A_l$ or the negative signal area $-A_l$ above threshold are significantly large, then a Category III defect exists in that frame. Shown figuratively:

| Lanes | $E_l$ | | $+A_l$ | | $-A_l$ | | $C_{3l}$ |
|---|---|---|---|---|---|---|---|
| 1 | 1 | | 0 | | 0 | | 0 |
| 2 | 0 | | 0 | | 1 | | 0 |
| 3 | 0 | And | 1 | Or | 0 | = | 0 |
| 4 | 0 | | 0 | | 1 | | 0 |
| 5 | 1 | | 0 | | 1 | | 1 |
| etc. | | | | | | | |

The above results show that a Category III defect exists in lane 5 in that frame of 80 scans.

The preferred embodiment of feature processor/discriminator 60, 61 uses DEC M logic modules and register transfer modules (RTM) (although micro-processor components are equally applicable) which are operated to function in the sequence shown according to the control section block diagram of FIG. 5. The control section is programmed to operate these elements in accordance with the ordered tasks detailed in the Table below. The flow diagram of FIG. 6 augments FIG. 5 to show how even and odd lane data processing loops are operated alternately to enable the system to process signal scan feature data in the time it takes the scan to transit the width of one frame (approximately 28 microseconds). The entire sequence of 15 tasks is completed in 50 milliseconds for each frame, whereas collect scan data logic, Task 12, is cycled every 625 microseconds in synchronization with each scan. In this system, Task 12 is performed eighty times per frame. All other tasks are performed once per frame.

TABLE
FEATURE PROCESSOR CONTROLLED TASKS
(Ref. FIG. 5)

| TASK NO. | TASK NAME | DESCRIPTION OF TASK |
|---|---|---|
| 0 | Output | Transfers feature status words to PDP 8/E computer at end of frame (13 words) |
| 1 | Spare | Available for additional functions |
| 2 | Spare | Available for additional functions |
| 3 | Spare | Available for additional functions |
| 4 | Spare | Available for additional functions |
| 5 | Spare | Available for additional functions |
| 6 | Spare | Available for additional functions |
| 7 | Spare | Available for additional functions |
| 8 | Edges $E_l$ | Compares edge count/frame against edge count threshold and sets lane bit in edge status word if threshold is exceeded |
| 9 | −Area (2) $A(2)_l$ | Compares −Area(2)/frame against −Area(2)/frame threshold and sets bit in −Area(2) status word if threshold is exceeded. |
| 10 | −Area(1) $-A(1)_l$ | Compares −Area(1)/frame against −Area(1)/frame threshold and sets bit in −Area(1) status word if threshold is exceeded. |
| 11 | +Area(1) $+A(1)_l$ | Compares +Area/frame against +Area/frame threshold and sets bit in +Area/frame status word if threshold is exceeded. |
| 12 | Take Data | Sums each scan feature to form frame feature, e.g., $\sum_{n=1}^{80} e_{1n} = E_l$ where $e_{1n}$ = edges/scan $E_l$ = edges/frame |
| 13 | Zero 3SP | Sets all scratch pad 3 memory locations to zero before starting new frame. |
| 14 | Zero 2SP | Sets all scratch pad 2 memory locations to zero before starting new frame. |
| 15 | Zero 1SP | Sets all scratch pad 1 memory locations to zero before starting new frame. |

FIG. 6 is a flow chart showing the operations occurring during Task 12, which is the data collection task. Note that two identical control strings are used, one for odd lanes and one for even lanes. These strings are operated alternately. The odd lane string interrogates the odd lane feature extraction circuitry while the even lane circuits are collecting data. The operation is then reversed as the scan across the next lane begins. Flip-flop, 302a, controls which lane string is being traversed. Each string is traversed eight times per scan, and the entire task eighty times per frame.

The flow chart notation used follows standard convention which specifies that the destination is stated first, the source second, and the operation contained in the source portion of the statement. Hence A←A+B is interpreted as: location A gets the sum of the contents of register A plus contents of register B.

The flow charts shown in FIG. 5 and FIG. 6 can be implemented using digital computers of any type with sufficient speed to perform the operations described in the available time. The implementation used in this preferred embodiment is a hardwired digital system built of DEC RTM components.

Before the product web passes through the inspection system, the operator enters the style data into computer memory through keyboard 110. The style data includes the frame and single-scan threshold values to be applied separately to the reflection and transmission channels and their associated feature processor/discriminators. These thresholds may include:

+high amplitude (max. allowable signal swing in (+) direction)

−high amplitude (max. allowable signal swing in (−) direction)

−defect duration (max. allowable duration of signal exceeding max. allowable swing in (−) direction)

+defect duration (max. allowable duration of signal exceeding max. allowable swing in (+) direction)

+A (max. allowable signal area exceeding positive threshold/frame)

−A (max. allowable signal area exceeding negative threshold/frame)

Edges (max. allowable total/frame)

−$A_2$ (intermediate level of area/frame between −A and +A)

+low amplitude (max. allowable swing in + direction between + high amplitude and + low amplitude values).

As previously noted, the (+) high amplitude threshold in the transmission channel relates to Category I defects which are defined as holes or very thin spots in the web. These will produce voltage peaks in the product signal of very high amplitude. Since the output of the plus high amplitude discriminator is connected to the plus defect duration detector, the two thresholds, namely (+) high amplitude and (+) defect duration, will work jointly to detect Category I defects greater than a specified minimum size without further feature processing. Similarly, a (−) high amplitude threshold in the transmission channel relates to Category II defects identified by large magnitude negative going voltage excursions caused by thick spots in the web such as jet spits, creases, and wrinkles. Since the minus high amplitude circuit is connected to the minus defect duration detector with its own threshold, small defects will be passed and those larger than a given size detected, again without the need for additional feature processing.

After all styling data has been entered, the inspection system is put into operation when the enabled product gate generator produces a signal waveform J to initiate the data collecting and processing operations.

A real time display of defect data appears on the CRT screen of input unit 110. The display can be arranged in columnar form such that the first column indicates the yardage along the web where an identified defect starts and ends, and the remaining columns represent the lanes across the web with symbols appearing therein to indicate the MD location and category of defect identified according to the feature and defect category of defect category correspondents. Simultaneously, line printer 100 can be used to produce a hard copy defect map showing the yardage of the start and end of each defect and its lane location. Finally, a roll summary is printed at the end of each run stating the total yardage containing unacceptable defects and the percent roll length which is defective.

Thus there is provided by this invention an on-line high speed web inspection system that determines the location and extent of classified defective portions on the web in real time using a unique feature extraction and pattern classification technique. By analyzing separately the composition of each frame of scans, approximating the size of the defects to be categorized, signal to noise ratios are improved, and rapid defect classification based on the web's optical properties is achieved.

What is claimed is:

1. An inspection system for web materials that includes electronic means responsive to means scanning the web for detecting a plurality of different nonuniform appearance features of the web, said electronic means comprising: means for electrically discriminating said appearance features as to a predefined class to identify the significant electrical signal components thereof; means for electrically dividing the web into frames; means for counting the number of occurrences of said significant signal components over a series of scans within each of said frames; means for comparing each count of the number of occurrences of said significant signal components within each frame with predetermined values to electrically define nonuniform appearance features according to frame; and means for combining said electrically defined nonuniform features to recognize the occurrence of a visual defect class as it occurs within each said scanned frame.

2. In an inspection system for web materials that includes electronic means responsive to means scanning the web for detecting a preselected plurality of different nonuniform appearance features of the web to form an extracted single-scan feature set, the improvement comprising: circuit means for dividing the web into separate but overlapping frames aligned in the web motion direction and transverse thereto; circuit means to accumulate in separate sums the respective values of the extracted single-scan features of said preselected plurality occurring in each said overlapping frame; means for discriminating said separate sums; means for composing respective binary lane feature status words from said discriminated sums, wherein each status word has a bit position assignment corresponding to the lane in which a significant appearance feature occurs; means for combining according to lane the bits of said lane feature status words into a predetermined logic statement, said logic statement defining a distinctive defect class; and means for determining the presence of said defect class according to the resultant truth value of said logic statement pertaining to each said frame.

3. In a method of inspecting a web that includes electro-optically scanning the web and generating electrical output signals representative of different nonuniform appearance features of the web and discriminating said output signals to form signals representing extracted single-scan features, the improvement comprising: electrically dividing the web into separate overlapping frames; accumulating in separate sums the respective values of said extracted single-scan features in each said overlapping frame; discriminating said separate sums to form binary lane feature status words; combining the bits of said lane feature status words into a predetermined logic statement, said logic statement defining a distinctive defect class; and determining the presence of said defect class according to the resultant truth value of said logic statement pertaining to each said frame.

* * * * *